United States Patent
Perritti et al.

(10) Patent No.: US 6,858,579 B2
(45) Date of Patent: Feb. 22, 2005

(54) ANTI-INFLAMMATORY COMPOUNDS

(75) Inventors: Mauro Perritti, London (GB); Roderick Flower, Langley (GB)

(73) Assignee: William Harvey Research Limited, London (GB)

( * ) Notice: Subject to any disclaimer, the term of this patent is extended or adjusted under 35 U.S.C. 154(b) by 462 days.

(21) Appl. No.: 09/759,484

(22) Filed: Jan. 12, 2001

(65) Prior Publication Data

US 2003/0171297 A1 Sep. 11, 2003

(51) Int. Cl.$^7$ .............................................. C07K 14/00
(52) U.S. Cl. ......................................... 514/2; 530/300
(58) Field of Search ................................ 530/350, 300; 514/2

(56) References Cited

U.S. PATENT DOCUMENTS 4,950,646 A  8/1990  Wallner et al.

OTHER PUBLICATIONS

Seemann et al. 1996; Molecular Biology of the Cell 7:1359–1374.*

L.H. Lim et al., Promoting detachment of neutrophils adherent to murine postcapillary venules to control inflammation: Effect of lipocortin1, Proceedings of the National Academy of Sciences of the United States of America, 1998, 95(24), 14535–9.

J.D. Croxtall et al., N–Terminal Peptide fragments of Lipocortin–1Inhibit A549 Cell Growth and Block EGF–Induced Stmulation of Proliferation, International Journal of Cancer, 1993, 54(1), 153–8.

M. Perretti et al., Lipocortin–1 Fragments Inhibit Neutrophil Accumulation and Neutrophil–Dependent Edema in the Mouse, Journal of Immunology, 1993, 151(8), 4306–14.

Croxtall et al., Inhibitory effect of peptides derived from the N–terminus of lipocortin 1 on arachidonic acid release and proliferation in the A549 cell line: identification of E–Q–E–Y–V as a crucial component, British Journal of Pharmacology, 1998, 123, 975–983.

Oxford Dictionary of Biochemistry and Molecular Biology, Oxford University Press 1997, pp. 537–538.

I.T. Paulsen et al., Characterisation of *sin*, a potential recombinase–encoding gene from *Staphylococcus aureus*, Gene, 1994, 141, 109–114.

P. Dezelee et al., Small Deletion in *v–src* SH3 Domain of a Transformation Defective Mutant of Rous Sarcoma Virus Restores Wild Type Transforming Properties, Virology, 1992, 189, 556–567.

* cited by examiner

*Primary Examiner*—Karen Cochrane Carlson
(74) *Attorney, Agent, or Firm*—Mathews, Collins, Shepherd & McKay, P.A.

(57) ABSTRACT

According to the present invention, there is provided a compound comprising the amino acid sequence AMVSE, wherein said compound does not comprise the amino acid sequence EQEYVQTV. Preferably the compound contains 5–11 amino acids. The compound is used in the manufacture of a medicament or pharmaceutical composition for inhibiting leukocyte migration, or treating or preventing inflammation and/or inflammatory response/disease from such conditions as gout, gouty arthritis, rheumatoid arthritis, asthma, reperfusion injury or damage, stroke, myocardial infarction, septic shock, or a skin disorder.

11 Claims, 2 Drawing Sheets

SEQUENCE LISTING

<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 1

Glu Gln Glu Tyr Val
  1               5

<210> SEQ ID NO 2

-continued

```
<211> LENGTH: 8
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 2

Glu Gln Glu Tyr Val Gln Thr Val
 1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 3

Ala Met Val Ser Glu
 1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 4

Ala Met Val Ser Glu Phe Leu Lys Gln Ala Trp
 1               5                  10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 5

Ser Val Glu Met Ala
 1               5

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 6

Ala Met Val Ser Glu Phe Leu Lys Gln Ala Trp Phe Ile Glu Asn Glu
 1               5                  10                  15

Glu Gln Glu Tyr Val Gln Thr Val Lys
             20                  25

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: synthetic
      sequence
```

-continued

```
<400> SEQUENCE: 7

Phe Ile Glu Asn Glu Glu Gln Glu Tyr Val Gln Thr Val
 1               5                  10

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: synthetic
      sequence

<400> SEQUENCE: 8

Phe Leu Lys Gln Ala Trp
 1               5
```

ANTI-INFLAMMATORY COMPOUNDS

TECHNICAL FIELD

The present inventions relates to compounds having anti-inflammatory properties.

BACKGROUND OF THE INVENTION

Inflammation at wound sites and sites of infection is often characterized by, inter alia, a strong infiltration of leukocytes at the site of inflammation. In particular, polymorphonuclear cells (PMN) are the predominant cell type recovered from the sites of inflammation, such as inflammatory joints (inflamed intraarticular and periarticular spaces) (Terkeltaub, 1992; Dieppe et al., 1979).

Inflammation can be reduced by the action of, for instance, such anti-inflammatory agents as glucocorticoids, produced by the body in response to inflammation. One of the many actions carried out by glucocorticoids is the induction of lipocortin 1 (LC1), which itself inhibits arachidonic acid release and cell proliferation (processes usually associated with inflammation).

The reviewed experimental evidence (Flower and Rothwell, 1994) supports the concept that lipocortin (LC) 1 is a key mediator of many effects of glucocorticoids including the suppression of lipid mediator release (Cirino et al., 1987) the inhibition of fever, (Carey et al., 1990; Davidson et al., 1991), paw oedema (Cirino et al., 1989) and poly-morphonuclear leukocyte (PMN) migration (Perretti et al., 1993), the inhibition of the release of adrenocorticotrophic hormone (ACTH) (Taylor et al., 1993) and other anterior pituitary hormones (e.g. Taylor et al., 1993, 1995) and the inhibition of the induction by endotoxin of nitric oxide synthase (Wu et al., 1995).

LC1 is a member of a super-family of proteins termed the annexins (reviewed by Raynal and Pollard, 1994). Members of this protein group are identified by a common structural motif comprising four repeating subunits (in some members of the family, eight repeating subunits). While this core domain is highly conserved amongst members of the annexin family each of the individual proteins has a distinct N-terminal domain of variable length and it has been suggested that since this is a distinguishing feature, it probably contributes to the biological activity specifically associated with each member. Indeed, previous work has demonstrated that LC1 lacking the N-terminal domain is without activity in some assays of inflammation and mediator release, whereas the full length N-terminus N-acetyl LC12–26 is biologically active in several systems (Cirino et al., 1993; Perretti, 1994).

The A549 cell line is a useful model for studying LC1 biology. The inhibitory action of glucocorticoids on cell proliferation in this model seems to be mediated by the induction and externalization of LC1, which subsequently impairs arachidonic acid release and therefore the release of eicosanoids which function as autocrine growth stimulators in this cell system (Croxtall and Flower, 1992). The gluco-corticoid block of arachidonic acid release and cell growth may be neutralized by anti-LC1 neutralizing monoclonal antibodies (Croxtall and Flower, 1992; Croxtall et al., 1995) or antisense deoxynucleotides (Croxtall and Flower, 1994), thus confirming the central role for this protein in glucocorticoid action.

In previous publications (Croxtall et al., 1993), it has been demonstrated that the N-terminal domain of LC1 is crucial in exerting this inhibitory effect on A549 cell function and that this biological property seems to reside in the downstream portion of the N-terminal domain ($LC1_{13-25}$) as $LC1_{1-12}$ is inactive in this model.

To define further the region necessary for the biological activity of the lipocortin N-terminal domain, experiments were carried out where a family of 25 peptides was synthesized in which systematic deletions were made from the N- and C-termini. This enabled a search to be carried out with more precision for the biological active region of the molecule (Croxtall et al., 1998). The results of these studies highlighted the importance of the domain EQEYV (SEQ ID NO:1), as a highly conserved sequence presenting all active peptides. The shortest peptide, which produced significant inhibitory activity, was $LC1_{18-25}$ (EQEYVQTV (SEQ ID NO:2)), implying that the domain EQEYV (SEQ ID NO:1), while essential, was not sufficient for biological activity.

However, the studies carried out by Croxtall and colleagues (Croxtall et al., 1998) were based upon an in vitro assay where cell division was measured.

Surprisingly, it has now been found that the in vivo anti-inflammatory properties of LC1 are contained within a different part of the N-terminal amino acid sequence of LC1, specifically $LC1_{2-6}$, (N-acetyl $LC1_{2-6}$=AMVSE (SEQ ID NO:3)).

SUMMARY OF THE INVENTION

According to the present invention, there is provided a compound comprising the amino acid sequence AMVSE (SEQ ID NO:3), wherein said compound does not comprise the amino acid sequence EQEYVQTV (SEQ ID NO:2).

Also provided by the present invention is a pharmaceutical composition which comprises a compound comprising the amino acid sequence AMVSE (SEQ ID NO:3), wherein said compound does not comprise the amino acid sequence EQEYVQTV (SEQ ID NO:2), and which further comprises one or more pharmaceutically acceptable excipients. Examples of such excipients include phosphate buffered saline (PBS) at, for example, 0.1 M, pH 7.4, $NaHCO_3$ at, for example, 0.2 M and other such physiologically acceptable fluids.

The present invention also provides the use of a compound comprising the amino acid sequence AMVSE (SEQ ID NO:3), wherein said compound does not comprise the amino acid sequence EQEYVQTV (SEQ ID NO:2), in the manufacture of a medicament for inhibiting leukocyte migration, or treating or preventing inflammation and/or inflammatory response/disease.

Yet further provided by the present invention is a method of inhibiting leukocyte migration, or treating or preventing inflammation and/or inflammatory response/disease, comprising administering to an animal an effective amount of a compound comprising the amino acid sequence AMVSE (SEQ ID NO:3), wherein said compound does not comprise the amino acid sequence EQEYVQTV (SEQ ID NO:2).

The present invention may employ any compound comprising the amino acid sequence AMVSE (SEQ ID NO:3) provided it does not comprise the amino acid sequence EQEYVQTV (SEQ ID NO:2). Preferably, the compound is a polypeptide. The polypeptide may be acyclic or cyclic.

The polypeptide may comprise any number of amino acid residues provided that it includes the sequence AMVSE (SEQ ID NO:3) but does not include the sequence EQEYVQTV (SEQ ID NO:2). Preferably, the polypeptide comprises 5–30, preferably 5–20, more preferably 5–11 amino acids. Preferably, the polypeptide comprises AMVSEFLKQAW (SEQ ID NO:4).

The compound may also include additional amino acid sequences or chemical groups flanking the amino acid sequence AMVSE (SEQ ID NO:3), wherein the additional sequences or groups enhance the anti-inflammatory properties of the compound.

Reference to "inflammation" or "inflammatory response/disease" refers to any inflammatory response or disease, including gout, gouty arthritis, rheumatoid arthritis, asthma, reperfusion injury or damage, stroke, myocardial infarction, septic shock, or an inflammatory skin disorder, such as psoriasis or eczema.

The present invention also provides the use as described above, wherein the medicament includes one or more pharmaceutically acceptable excipients.

The present invention also provides the method as described above, wherein a composition which comprises a compound comprising the amino acid sequence AMVSE (SEQ ID NO:3), wherein said compound does not comprise the amino acid sequence EQEYVQTV (SEQ ID NO:2), and which further comprises one or more pharmaceutically acceptable excipients is administered to an animal.

DETAILED DESCRIPTION OF THE INVENTION

The present invention will now be described, by way of example only, with reference to the accompanying figures, wherein.

Figure 1:
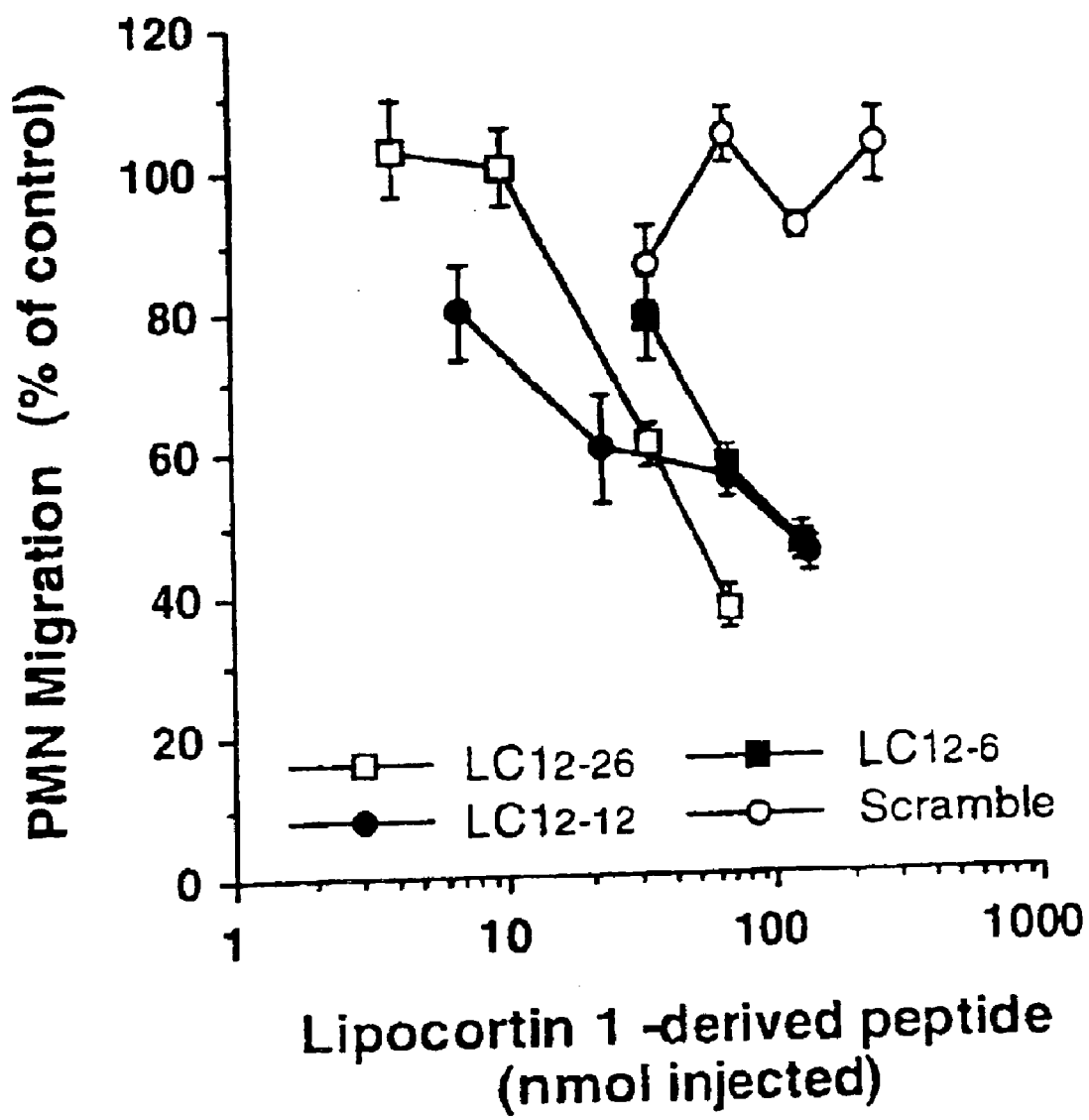
FIG. 1 illustrates the degree of inflammatory response (as measured by PMN migration) generated by the in vivo activity of lipocortin 1-derived peptides (Scramble=LC1$_{2-6}$ (Ac-SVEMA (SEQ ID NO:5)); Ac=acetyl).

The in vivo anti-inflammatory properties of the amino acid sequence AMVSE (SEQ ID NO:3) were demonstrated by preparing fragments of N-acetyl LC1$_{2-26}$ (AMVSEFLKQAWFIENEEQEYVQTVK (SEQ ID NO:6)) and testing them in an animal model of inflammation. The in vivo animal model provided evidence that while N-acetyl LC1$_{2-2}$ (AMVSEFLKQAW ((SEQ ID NO:4))) was active in the model, LC1$_{13-25}$ (FIENEEQEYVQTV (SEQ ID NO:7)) was not (data not shown). When AMVSE (SEQ ID NO:3) and LC1$_{7-12}$ (FLKQAW (SEQ ID NO:8)), were tested the former was active whereas the latter was not. A scrambled version of AMVSE (SEQ ID NO:3) (namely, SVEMA (SEQ ID NO:5)) was also found to be inactive.

The experiments described herein clearly indicate that the biological properties of lipocortin 1 (LC1) differ in in vivo inflammatory models compared to the in vitro A549 model.

The compounds used in the present invention are preferably prepared for use as pharmaceuticals. The polypeptides may be administered by any suitable route including oral or parenteral administration. Pharmaceutical compositions, which comprise the compounds described typically, will contain diluents, such as water, saline, glycerol, ethanol, etc. Additionally or alternatively, auxiliary substances, such as wetting or emulsifying agents, pH buffering substances, and the like, may be present in such vehicles. The polypeptide-containing compositions are preferably administered in combination with pharmaceutically acceptable excipients such as 0.1 M PBS (pH 7.4), 0.2 M NaHCO$_3$ or other such pharmaceutically acceptable fluids.

Typically, the compositions contemplated are prepared as injectables, either as liquid solutions or suspensions; solid forms suitable for solution in, or suspension in, liquid vehicles prior to injection may also be prepared. The preparation also may be emulsified or encapsulated in, for example, liposomes.

Compositions used as pharmaceuticals comprise an effective amount of the compound, as well as any other of the above-mentioned components, as needed. By "effective amount", it is meant that the administration of that amount to an individual, either in a single dose or as part of a series, is effective for treatment or prevention. This amount varies depending upon the health, age and physical condition of the individual to be treated, the taxonomic group of individual to be treated (e.g., non-human primate, primate, etc.), the treating doctor's assessment of the medical situation, and other relevant factors. The amount falls in a relatively broad range that can be determined through routine trials. Typical dosages may fall within the range 0.1–100 mg/kg, preferably 0.5–50 mg/kg, most preferably 1–10 mg/kg.

The compositions contemplated are conventionally administered parenterally, e.g. by injection either subcutaneously or intramuscularly. Additional formulations suitable for other modes of administration include oral and pulmonary formulations, suppositories and transdermal applications. Dosage treatment may be a single dose schedule or a multiple dose schedule. The composition may be administered in conjunction with other anti-inflammatory agents.

As used herein, the term "polypeptide" refers to a polymer of amino acids and is not limited to a specific length of the molecule; thus, peptides, oligopeptides, and proteins are included within the definition of polypeptide. The polypeptide may be produce by chemical synthesis or by recombinant DNA techniques well known to persons skilled in the art. The term "polypeptide" also includes modifications of the polypeptide, for example, glycosylations, acetylations, phosphorylations, cyclisations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring.

The present invention will now be described with reference to the following rig examples. It will be appreciated that the following is provided by way of example only and modification of detail may be made without departing from the scope of the invention.

EXPERIMENTAL PROTOCOL

Animals

Male Swiss Albino mice (20–22 g body weight) were purchased from Interfauna (CFLP strain; Huntingdon, Cambridgeshire, UK) and maintained on a standard chow pellet diet with tap water ad libitum. Animals were used at least one week after arrival.

Mouse Air-Pouch Model

Air-pouches were formed on the back of the mice by subcutaneous (s.c.) injection of 2.5 ml or air on day 2 and day 5. Three days after the last air-injection (6-day-old air-pouches) 1 mg of zymosan (in 0.5 ml of sterile saline) was injected locally (Perretti et al., 1996). Zymosan was previously boiled for 30 min in phosphate buffered solution (PBS), extensively washed in the same medium and stored at −20° C. prior to use.

Four hours after the local injection of zymosan, mice were killed by $CO_2$ exposure and the air-pouches washed with 2 ml of PBS containing ethylenediaminetetracetic acid sodium salt (EDTA; 3 mM) and heparin (25 U/ml).

Lavage fluids (essentially the entire 2 ml were consistently recovered) were centrifuged at 200 g for 10 min at 4° C. and cell pellets were resuspended in 2 ml of PBS/EDTA+ heparin. The number of PMN was determined, using a Neubauer haematocytometer, after staining (1:10 dilution) with Turk's solution (crystal violet 0.01% w/v in acetic acid 3% v/v).

Peptides

All peptides were synthesized following conventional solid phase technique by the Advanced Biotechnology Center, Charing Cross Westminster Medical School (London, UK) and purified by high liquid performance chromatography. All peptides were more than 95% pure.

Drug Treatment

The following peptides were drawn from the lipocortin 1 N-terminus region: $LC1_{2-26}$ (Ac-AMVSEFLKQAWFIENEEQEYVQTVK (SEQ ID NO:6)), $LC1_{2-12}$ (Ac-AMVSEFLKQAW (SEQ ID NO:4)), $LC1_{13-25}$ (FIENEEQEYVQTV (SEQ ID NO:7)), $LC1_{2-6}$ (Ac-AMVSE ((SEQ ID NO 3))), or scramble $LC1_{2-6}$ (AC-SVEMA (SEQ ID NO:5)) were administered s.c. 30 min prior to injection of 1 mg zymosan into the air-pouches. Control mice were treated with sterile PBS (100 µl s.c.).

Results

FIG. 1 shows that of the fragments of $LC1_{2-26}$, $LC1_{2-12}$ and $LC1_{2-6}$ showed the greatest potency, having almost identical final percentage inhibition responses. Data are shown as percentage of control inhibition of PMN migration, which is the leukocyte extravasations measured in vehicle (sterile PBS)-treated mice. Approximate $ED_{50}$s of 45, 110 and 110 nmol were calculated (n=15; P<0.01), respectively.

$LC1_{2-26}$ itself showed the greatest potency. This is likely to be due to the presence of residues flanking the AMVSE (SEQ ID NO:3) sequence that increase the PMN migration inhibitory activity of the pharmacore AMVSE (SEQ ID NO:3).

Figure 2:
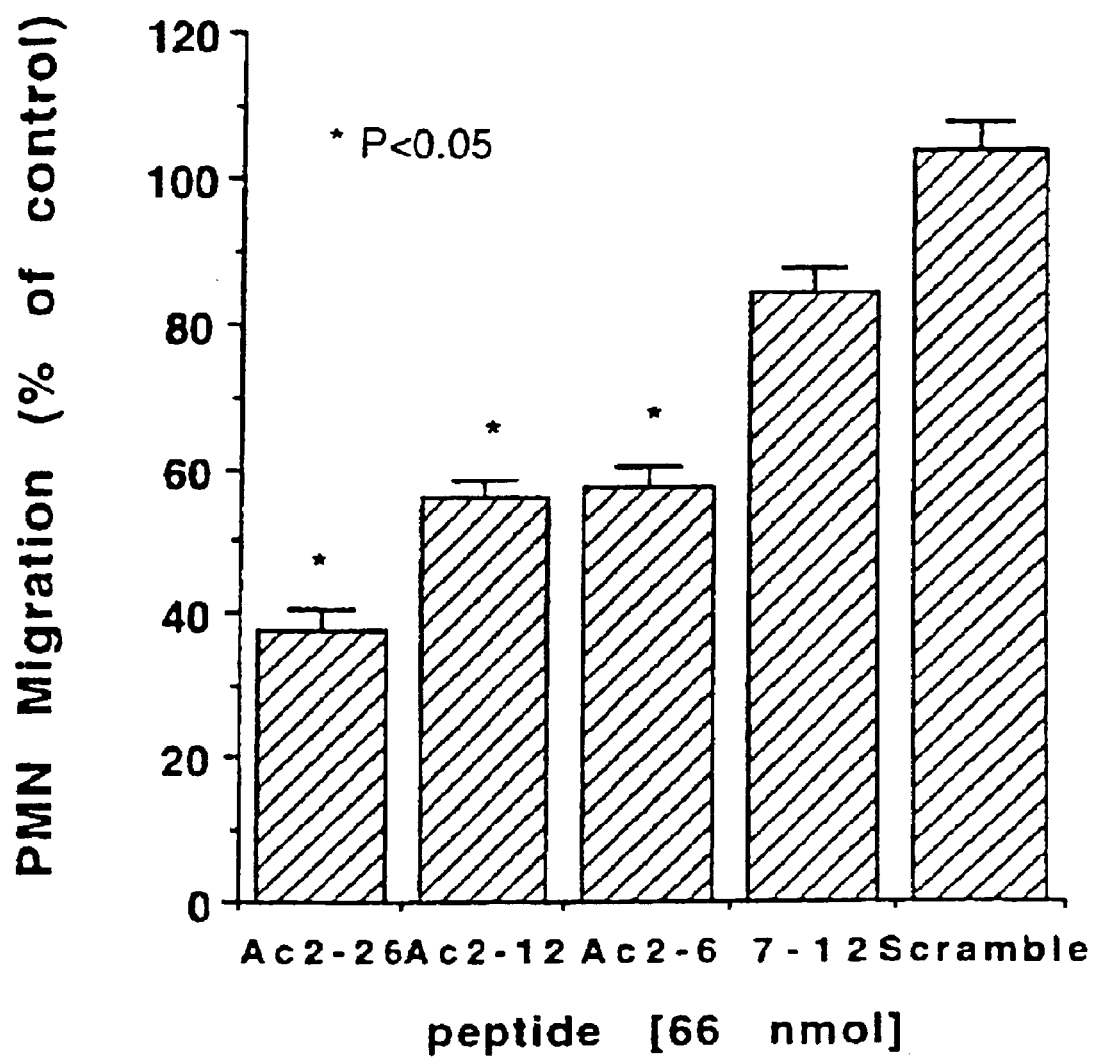
FIG. 2 illustrates (as a bar chart) the degree of inflammatory response (as measured by PMN migration) generated by the in vivo activity of 66 nmol lipocortin 1-derived peptides with reference to FIG. 1 (Scramble=LC1$_{2-6}$ (Ac-SVEMA (SEQ ID NO:5)); Ac=acetyl).

FIG. 2 reports the inhibitory action of an equimolar dose of the recited peptides, and indicates that the activity found in $LC1_{2-12}$ is contained within the $LC1_{2-6}$ domain.

The results clearly indicate the inhibitory effect of the AMVSE (SEQ ID NO:3) pharmacore on PMN migration and the possibility of its enhanced potency in combination with suitable flanking sequences. The AMVSE (SEQ ID NO:3) pharmacore represents the minimum active sequence from which further useful sequences may be derived by combining the core AMVSE (SEQ ID NO:3) sequence with additional flanking sequences, chemical groups designed to improve the binding or penetration of the peptide to its active site or other chemical groups that in some other way improve the anti-inflammatory properties of a compound comprising the pharmacore AMVSE (SEQ ID NO:3)

REFERENCES

Carey, F. et al., *Am. J. Physiol.*, 259: 266–269 (1990).
Cirino, G. et al., *Nature*, 328: 270–272 (1987).
Cirino, G. et al., *Proc. Natl. Acad. Sci. USA*, 86: 3428–3432 (1989).
Cirino, G. et al., *British Journal of Pharmacology*, 108: 573–574 (1993).
Croxtall, J. D. and Flower, R. J., *Proc. Natl. Acad. Sci. USA*, 89: 3571–3575 (1992).
Croxtall, J. D. and Flower, R. J., *Biochem. Pharmacology*, 48: 1729–1734 (1994).
Croxtall, JD. et al., *Int. J. Cancer*, 54: 153–158 (1993).
Croxtall, JD. et al., *Biochem. Pharmacol.*, 50: 465474 (1995).
Croxtall, J. D. et al., *British Journal of Pharmacology*, 123: 975–983 (1998).
Davidson, J. et al., *British Journal of Pharmacology*, 102: 7–9 (1991).
Dieppe, P. A. et al., *Q. J. Med.*, XLVIII: 533–553 (1979).
Flower, R. J. and Rothwell, N. J., *Trends Pharmacol. Sci.*, 15: 71–76 (1994).
Perretti, M. et al., *J. Immunol.*, 151: 4306–4314 (1993).
Perretti, M., *Biochem. Pharmacology*, 47: 931–938 (1994).
Perretti et al., *British Journal of Pharmacology* 117: 1145–1154 (1996).
Raynal, P. and Pollard, H. B., *Biochim. Biophys. Acta.* 1197: 63–93 (1994).
Taylor, A. D. et al., *Neuroendocrinology*, 58: 430–439 (193)*
Taylor, A. D. et al., *J. Endocrinol.*, 147: 533–544 (1995).
Terkeltaub, R., "Gout. Crystal-induced inflamnmation", in: *Inflammation. Basic Principles and Clinical Correlates*, edited by Gallin, J. I. et al., pp. 977–981, Raven Press, New York (1992).
Wu, C.-C. et al., *Proc. Natl. Acad. Sci. USA*, 92: 3473–3477 (1995).

What is claimed is:

1. An isolated compound for use in pharmaceutical therapy comprising SEQ ID NO:3, wherein said compound does not comprise SEQ ID NO:2, and contains 5–11 amino acids.

2. A compound according to claim 1, which is a polypeptide.

3. A compound according to claim 2, which comprises SEQ ID NO:4.

4. A compound according to claim 1 which is effective in inhibiting leukocyte migration in a mammal.

5. A compound according to claim 1 which is effective in treating or preventing inflammatory response in a mammal.

6. A compound according to claim 5 which is effective in treating or preventing inflammation in a mammal.

7. A pharmaceutical composition comprising a compound which comprises SEQ ID NO:3, wherein said compound does not comprise SEQ ID NO:2, and contains 5–11 amino acids, and which composition comprises one or more pharmaceutically acceptable excipients.

8. A pharmaceutical composition according to claim 7 comprising an effective amount of said compound to inhibit leukocyte migration when administered to a mammal.

9. A method of manufacture of a pharmaceutical composition, comprising:

combining a compound comprising SEQ ID NO:3, wherein said compound does not comprise SEQ ID NO:2, and which contains 5–11 amino acids, with a pharmaceutically acceptable excipient.

10. A method of treating or preventing an inflammatory response comprising administering to an animal an effective amount of a compound comprising SEQ ID NO:3, wherein said compound does not comprise SEQ ID NO:2.

11. The method according to claim 10, wherein the inflammatory response is gout, gouty arthritis, rheumatoid arthritis, asthma, reperfusion injury or damage, stroke, myocardial infarction, septic shock, or a skin disorder.

* * * * *